United States Patent [19]

Abrams

[11] Patent Number: 4,466,445

[45] Date of Patent: Aug. 21, 1984

[54] SYSTEMS AND DEVICES FOR MEASUREMENT OF URINE TEMPERATURE, PARTICULARLY FOR DETECTING THE SHIFT IN BASAL BODY TEMPERATURE IN WOMEN

[75] Inventor: Robert M. Abrams, Gainesville, Fla.

[73] Assignee: University of Florida, Gainesville, Fla.

[21] Appl. No.: 418,657

[22] Filed: Sep. 16, 1982

[51] Int. Cl.³ ............................................. G01N 33/16
[52] U.S. Cl. .................................... 128/736; 128/738; 128/761; 374/157
[58] Field of Search ............... 128/736, 738, 760, 761, 128/767; 374/141, 157, 208

[56] References Cited

PUBLICATIONS

U.S. application Ser. No. 359,899–Elias Filed Mar. 15, 1982.
J. P. Royston and R. M. Abrams, "An Objective Method for Detecting the Shift in Basal Body Temperature in Women", *Biometrics*, vol. 36, No. 2, pp. 217–224, (Jun. 1980).
Burton-Fanning, F. W. & Champion, S. C., "The Comparative Value of the Mouth, the Rectum, the Urine, the Axilla, and the Groin for the Observation of the Temperature; Especially in Regard to Tuberculosis and to the Effects of Exercise and other Conditions", *The Lancet*, 1903, vol. 1, pp. 856–862.
Ellenbogen, C., and Nord, B., "Freshly Voided Urine Temperature: A Test For Factitial Fever", *Journal of the American Medical Association*, vol. 219, No. 7, p. 912 (1972).
Murray, H., Tuason, C., Guerrero, T., Claudio, M., Alling, D., and Sheagren, J., "Urinary Temperature–A Clue to Early Diagnosis of Factitious Fever", *The New England Journal of Medicine*, vol. 296, No. 1, pp. 23–24, (1977).
Sankey, E. T. P., "A Comparison of Oral Temperature Readings and Freshly Voided Urinary Specimen Temperature Determinations", Masters Thesis, University of Delaware, 1978, pp. v, vi, 18–21, 29, 30–32, 35–36.
Fox, R. H., Fry, A. J., Woodward, P., Collins, J. C. and MacDonald, I. C., "Diagnosis of Accidental Hypothermia of the Elderly", *The Lancet*, 1971, vol. 1, pp. 424–427.

*Primary Examiner*—Edward M. Coven
*Attorney, Agent, or Firm*—Kerkam, Stowell, Kondracki & Clarke

[57] ABSTRACT

An automatic system for recognizing a shift in basal body temperature indicative of the beginning of a period of infertility combines a device for measurement of urine temperature with a signal processing subsystem. Two specific forms of temperature measurement device are disclosed, and both are adapted for positioning in a toilet bowl.

27 Claims, 3 Drawing Figures

SYSTEMS AND DEVICES FOR MEASUREMENT OF URINE TEMPERATURE, PARTICULARLY FOR DETECTING THE SHIFT IN BASAL BODY TEMPERATURE IN WOMEN

BACKGROUND OF THE INVENTION

The present invention relates to accurate measurement of urine temperature upon micturation as an indication of body temperature, and to the use of such measurements as an aid in natural methods of birth control.

Natural Family Planning is based on the recognition of physiologic signs and symptoms which identify the fertile and infertile phases of the menstrual cycle. More particularly, one known method of natural birth control is based on a recognition that basal (waking) body temperature (BBT) in fertile women is variable, and normally follows a cyclical pattern, shifting upwardly near the middle of each menstrual cycle. Within a few days of the occurrance of the upward shift in temperature, sufficient time has elapsed from the occurrence of ovulation, and a period of infertility begins, knowledge of which may be utilized in a program of natural birth control.

Basal body temperature is obtained by taking a temperature measurement at a standard time which ideally is just after waking and before rising. The traditional approach involves taking daily basal body temperature readings with a conventional thermometer, recording the daily measurements in graphical form, and interpreting the graph in order to identify the occurrence of a significant upward shift in temperature.

It will be appreciated that the traditional manual approach is somewhat unreliable for a number of reasons. For one, the accuracy of the temperature reading is sometimes poor. Additionally, it is frequently difficult for the average person to decide when the upward shift in temperature has occured. Another reason for unreliability is that it is inconvenient for most women to take their temperature every day immediately on waking, enter the temperature reading on a graph, and spend some time studying that graph. Taking shortcuts when doing these steps compromises the quality and meaning of the results.

In short, there necessarily are human errors involved in any method requiring very accurate reading of an instrument, correct entry of data on a chart and interpretation of temperature trends.

Accordingly, it has previously been proposed to automate the entire measurement and computation process in a portable device. For example, Lester U.S. Pat. No. 4,151,831 discloses various forms of a microprocessor-based instrument including a sensor for taking temperature readings, a digital clock for indicating when a temperature reading is to be taken, a memory for storing daily temperature readings, and a programmed microprocessor computing system for interpreting the results and indicating to the user when a period of infertility has begun. Lester proposes various forms of temperature sensor, including vaginal and oral temperature probes, and a skin temperature sensor.

Another example is disclosed in published U.K. patent application No. 80.40786, filed 19 Dec. 1980, and published as No. 2,066,528 on 8 July 1981, claiming the benefit of U.K. patent application No. 79.44063 filed 21 Dec. 1979, naming as inventors Wolff, Abrams, Royston and Humphrey, and entitled "Measurement of Basal Body Temperature". The Wolff et al device includes a probe for daily oral temperature readings. In order to reliably, and on a statistical basis, recognize the upward shift in BBT indicative of the beginning of a period of infertility, the device disclosed in the above-identified Wolff et al U.K. publication No. 2,066,528 implements a cumulative sum (CUSUM) algorithm described in the literature: J. P. Royston and R. M. Abrams, "An Objective Method for Detecting the Shift in Basal Body Temperature in Women", *Biometrics*, Vol. 36, No. 2, pp. 217–224 (June 1980).

A more recent example of a system implementing the Royston et al CUSUM algorithm for recognizing an upward shift in BBT is disclosed in U.S. Pat. Application Ser. No. 357,899, filed Mar. 15, 1982, by Andre E. Elias, and entitled "Microprocessor-Based Instrument for Detecting Shift in Basal Body Temperature in Women". The Elias instrument also includes a probe for daily oral temperature readings and includes a number of refinements relating to lower power consumption facilitating battery operation and to improved verification procedures for recognizing invalid temperature readings.

The entire disclosures of both the above-identified U.K. patent publication No. 2,066,528 and the above-identified U.S. application Ser. No. 357,899 are hereby expressly incorporated by reference herein for their descriptions of portable devices capable of recording daily temperature measurements and implementing a CUSUM test to recognize an upward shift in BBT.

Underlying the development of the Royston et al algorithm described in the above-identified literature reference, and implemented in the devices described in the U.K. patent publication No. 2,066,528 and in the U.S. application Ser. No. 357,899, is the fact that, even with accurate daily temperature measurements, many charts depicting basal body temperature throughout a menstrual cycle do not display a sharp, clear-cut rise. Various different patterns of basal body temperature rise are found, some of which are quite difficult to interpret without benefit of hindsight. The Royston et al article describes a statistical method for detecting an upward shift in basal body temperature, which method is based on the cumulative sum (CUSUM) test previously employed in the context of quality control of production processes.

For its detailed description of the CUSUM test for detecting upward shift in basal body temperature, the above-identified Royston et al article entitled "An Objective Method for Detecting the Shift in Basal Body Temperature in Women" is hereby expressly incorporated by reference. However, in order that the present invention may be better understood, the Royston et al algorithm is next briefly summarized.

The general problem is to begin with a plurality of sample values $x_1, x_2 \ldots x_n, \ldots x_N$ of a random variable X. In the context of detecting an upward shift in BBT, each of the sample values $x_r$ is simply a daily temperature reading, appropriately corrected for time of day. It is then desired to detect an upward drift of the mean $E(X)$ above some baseline B. As pointed out in Royston et al, in general, menstrual cycles in which ovulation has occurred show a biphasic BBT pattern, with a shift from a low post-menstrual level to a higher level around the time of ovulation. Ovulation usually takes place about two weeks before the onset of the next menstrual period. Royston et al refer to temperatures at the lower post-menstrual level to be "pre-ovulatory", and those at the premenstrual higher level as "post-ovulatory", although it is acknowledged that the temperature change does not actually prove that ovulation has occurred.

The baseline temperature is taken as a simple average of a number of daily readings. For example, the baseline may be taken as a simple average of eight daily readings, commencing on the fourth day following the beginning of a menstrual period. Thus, these eight days may be considered to be a baseline period. Temperature readings for the first three days of a menstrual period are not considered valid because they are sometimes still elevated as a carryover from the previous cycle.

The actual CUSUM test for the purpose of detecting an upward shift begins following the baseline period. The temperature reading for each day is generally compared to the baseline temperature (or, more accurately, to a reference temperature R derived from the baseline temperature). Positive deviations are represented by $(x_r - R)$. The cumulative sum (CUSUM) of positive deviations eventually becomes significantly large.

In the details of the implementation, a minimum change term is statistically predetermined, the minimum change term being related to the minimum basal body temperature rise considered to be physiologically significant as indicating a shift truly representative of ovulation. As reported by Royston et al, this minimum BBT rise is approximately 0.2° C. and, for purposes of the CUSUM test, the predetermined minimum change term is 0.1° C.

For purposes of comparison during the CUSUM test, rather than the actual baseline average temperature, a "central reference value" is employed, which is simply the actual baseline average temperature plus the predetermined minimum change term, which is 0.10° C. This "central reference value" corresponds to the "reference temperature" R, introduced above.

The positive deviations $(x_r - R)$ are accumulated day by day, and their cumulative sum (CUSUM) compared to a decision interval, which is also statistically predetermined. By way of example the decision interval may be taken as 0.25° C. On a day when the cumulative sum of positive deviations exceeds the decision interval, the CUSUM test is satisfied, indicating that a period of infertility has commenced, and the user may stop taking daily temperatures until the start of the next menstrual period.

The present invention further improves the instruments summarized above through the selection of a particular temperature measurement "site", namely measurement of the temperature of freshly-voided urine. Moreover, the present invention provides improved devices for rapid, convenient, accurate and reliable measurement of urine temperature for any purpose.

Axillary, rectal, vaginal and oral temperature measurements have all shown the mid-cycle upward shift in waking temperature, but all of these common sites have disadvantages. The axilla is not reliable if women have had the axilla exposed prior to temperature recording. Caution is advised when inserting the thermometer in the vagina; there are reports of accidental insertion in the urethra and transport to the bladder. The rectum is most often recommended, yet many women find this site unacceptable. Oral sites are more acceptable but perhaps not as reliable. Additionally, the time required to prepare the thermometer, to insert and leave in place, to read and finally to enter the data on a chart is so long that all but the most diligent and motivated women become disinterested in the method.

It has previously been recognized that urine temperature is a reliable indicator of body temperature. For example, the comparative value of temperatures of the mouth, rectum, urine, axilla and groin were observed by Burton-Fanning et al as early as 1903. (See Burton-Fanning, F.W. and Champion, S.C., "The comparative value of the mouth, the rectum, the urine, the axilla, and the groin for the observation of the temperature; Especially in regard to tuberculosis and to the effects of exercise and other conditions", The Lancet, 1903, Vol. 1, pp. 856-862.) These researchers employed the simple method of having male subjects void two to five ounces directly over the bulb of a mercury thermometer. The researchers reported correct readings in a majority of cases when temperatures were compared to rectal temperatures.

More recent experiments have employed insulated containers. For example, experiments by Ellenbogen et al (1972) and Murray et al (1977) utilized an insulated cup to obtain and record urine temperature with a mercury thermometer in an attempt to diagnose factitious fever. Both studies revealed a highly significant correlation with rectal temperatures as well as with oral temperatures. (See Ellenbogen, C., and Nord, B. "Freshly voided urine temperature: A test for factitial fever", Journal of the American Medical Association, Vol. 219, No. 7, p. 912 (1972); and Murray, H., Tuason, C., Guerrero, T., Claudio, M., Alling, D., and Sheagren, J. "Urinary temperature -- A clue to early diagnosis of factitious fever", The New England Journal of Medicine, Vol. 296, No. 1, pp. 23-24, (1977).)

As another example, a comparison of oral and urine temperature in adult male cardiac patients was performed by Sankey as reported in 1978. An electronic thermometer probe was used and placed in a styrofoam cup prior to the initiation of micturition. Temperature measurements were recorded at one, two, four and eight minutes after the completion of voiding. Voided urine temperature at one minute was found to be 0.81 degrees Fahrenheit higher than oral temperatures, and rapid cooling then proceeded (See Sankey, E. T. P. "A comparison of oral temperature readings and freshly voided urinary specimen temperature determinations," Masters Thesis, University of Delaware, 1978.)

Of somewhat greater pertinancy in the particular context of the present invention is a urine temperature measurement bottle devised by Fox et al for use in diagnosing hypothermia in the elderly. (See Fox, R. H., Fry, A. J., Woodward, P., Collins, J. C. and MacDonald, I. C. "Diagnosis of accidental hypothermia of the elderly", The Lancet, 1971, Vol. 1, pp. 424-427)

The Fox et al device comprises a one-liter plastic bottle fitted with a thin plastic funnel insert supplying a small overflow reservoir. Urine is funneled over a standard clinical thermometer, with the reservoir ensuring that the tip of the thermometer remains immersed with low rates of urine flow. Twelve male subjects tested the device, and the authors reported consistent correlations between rectal and urine temperature for urine volumes between 50 ml and 100 ml. A female version of the device which could be fixed in position on the toilet was mentioned, but test results using the female device version were not presented.

SUMMARY OF THE INVENTION

In accordance with one overall concept of the invention, both method reliability and user compliance in the context of automated systems for detecting upward shift in BBT are improved by the combination of an automated device for measurement of urine temperature with an automatic decision-making and signaling device to alert women to the time when they can have unprotected intercourse with little fear of becoming pregnant. In the specific context of natural family planning there are at least two advantages of using voided urine to estimate body temperature: (1) Urinary bladder contents equilibrate with the temperature of the true core of the body; and (2) the thermal inertia of urine in the bladder resists rapid changes in early morning tissue temperature occasioned by moving about upon awakening. Thus the ideal of a temperature measurement taken after waking but before rising can in effect be realized, even though the temperature measurement is in actuality taken after rising.

More particularly, in accordance with the invention, there is provided a system for use by a human female on a daily basis upon awakening for the purpose of detecting an upward shift in basal body temperature indicative of the beginning of a period of infertility. The system includes a device for measurement of urine temperature upon micturation as an indicator of body temperature, the temperature measurement device including an electrical temperature sensing element. The system also includes a signal-processing subsystem electrically connected to the temperature sensing element and operable to record daily urine temperature readings indicated by basal body temperature, perform a statistical test for recognizing an upward shift in basal body temperature indicative of the beginning of a period of infertility, and signalling when the statistical test has been satisfied.

In one particular form, the device for measurement of urine temperature includes a funnel having a mouth for receiving urine and an apex, and a flow-through sensing portion positioned at the funnel apex for receiving urine. The flow-through sensing portion has a reservoir, and the reservoir has a flow-restricting drain aperture for the reservoir. Preferably, there is at least one overflow aperture for the funnel positioned between the funnel mouth and apex, and a baffle for the overflow aperture to initially direct urine towards said flow-through sensing portion. The electrical temperature sensing element is positioned within the reservoir.

In another form, the device for measurement of urine temperature comprises an inclined V-trough having sidewalls of thermally insulative material. Preferably, a dam is positioned generally at the downstream end of the inclined V-trough, the dam being relatively low in height compared to the sidewalls of the V-trough, and the dam thus defining an overflow reservoir within which the electrical temperature-sensing element is positioned. A plurality of ridges are provided on the V-trough sidewalls for directing urine towards the reservoir. Under some circumstances, particularly with a suitably-small temperature sensing element positioned in and generally at the downstream end of the inclined V-trough, it is sufficient to provide the plurality of ridges on the V-trough sidewalls, without need for the reservoir. This form of temperature measuring device depends upon sufficient urine flow to keep the temperature sensing element completely covered or immersed at all times, particularly where a temperature sensing element having a relatively short thermal time constant is employed, as is preferred for rapid measurement results.

The temperature-sensing element has a relatively short thermal time constant and, for example, may comprise a junction-type thermocouple coated with a thin electricallly-insulating layer of epoxy or similar material. Alternatively, the temperature-sensing element may comprise a thermistor. In either case, the relatively short thermal time constant results in two advantages. First, the entire measurement cycle is relatively fast, requiring essentially no additional time on the part of the user, and no inconvenience. Second, urine flow occurs for a relatively short period of time, typically less than twenty seconds. The short thermal time constant permits the temperature of the temperature-sensing element to be stabilized, and a temperature reading taken, well within this twenty-second time interval.

For greatest utility, either of the particularly-disclosed forms of temperature measuring device includes a support structure for positioning the temperature measuring device within a toilet bowl. The signal-processing subsystem is then located conveniently nearby, preferably, attached to the toilet bowl.

It will be apparent that the present invention is not directed to the details of the signal-processing subsystem itself, as either the system disclosed in the above-identified Wolff et al U.K. patent publication No. 2,066,528 or the Elias U.S. Pat. application Ser. No. 357,899 may be employed, with minor modification. In particular, the signal-processing subsystem should be modified to give audio, rather than visual signals. The timing of the signal-processing subsystem must be altered to reflect the much shorter thermal time constant of the temperature-sensing element, since the unmodified signal-processing subsystem waits twenty seconds or more for an oral temperature probe to reach thermal equilibrium. Additionally, the input characteristics of the signal-processing subsystem must match the output characteristics of the temperature sensing element, taking into account that a junction thermocouple is a variable voltage generating device, while a thermistor is a variable resistance device.

The present invention, therefore, provides an overall system for detecting the shift in basal body temperature in women, which system promotes both method reliability and user compliance. Moreover, by the present invention two specific forms of temperature measuring device adapted for positioning within a toilet bowl are provided.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings, in which:

DETAILED DESCRIPTION OF THE PREFERRED EMBODIMENTS

Figure 1:
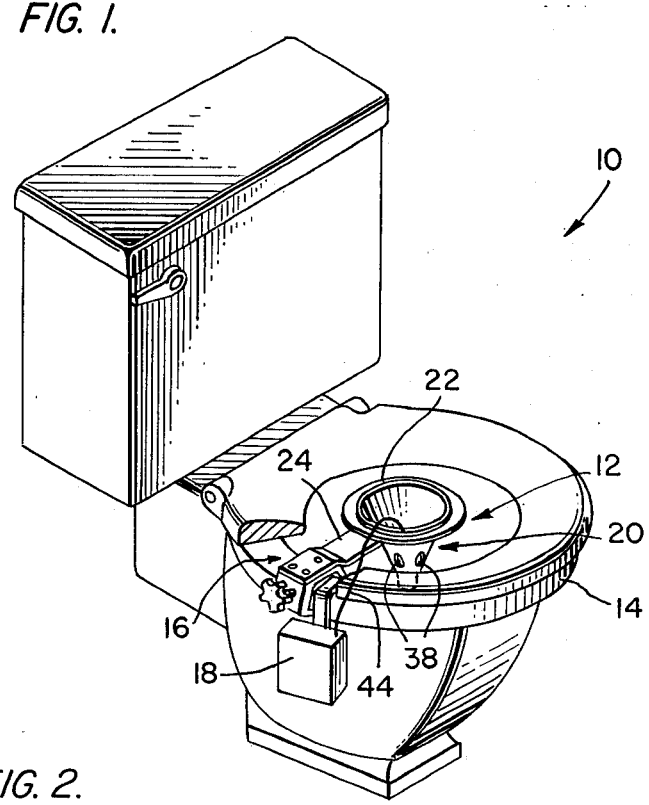
FIG. 1 depicts an overall view of a first form of urine temperature measurement device secured within a toilet bowl.

Referring first to FIG. 1, shown is an overall system 10 for use by a human female on a daily basis upon awakening for the purpose of detecting an upward shift in basal body temperature. The system 10 includes a device, generally designated 12, for measurement of urine temperature upon micturation as an indicator of body temperature. The device 12 is secured within a toilet bowl 14 by means of a clamping arrangement 16 secured to the rim of the toilet bowl 14.

Hanging beside or behind the bowl 14 is a signal-processing subsystem 18 within a suitable box, including a microprocessor, supporting peripherals, and batteries, as for example disclosed in either the above-identified incorporated Wolff et al. U.K. patent publication No. 2,066,528 or the Elias U.S. Pat. application Ser. No. 357,899, suitably modified as described briefly above in view of the relatively thermal time constant of the present system.

The form of temperature measuring device 12 of FIG. 1 generally comprises a funnel structure 20 supported within a circular holder 22 attached by means of an arm 24 to the clamping device 16.

Figure 2:
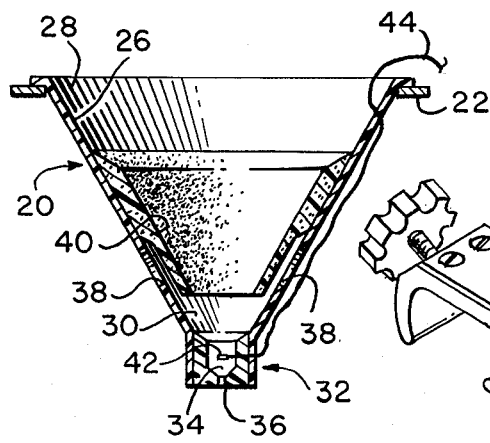
FIG. 2 is an enlarge cross-sectional view through a portion of the FIG. 1 device.

From FIG. 2 may be seen more particularly the details of the funnel-like device 20. In particular, the device 20 includes a funnel 26 having a mouth 28 for receiving urine, and an apex 30. Preferably, the walls of the funnel 26 are made of thermally-insulating material. While plastic may be employed, styrofoam is preferred in order to prevent cooling of the urine before temperature measurement.

Positioned at the funnel apex 30 is a flow-through sensing portion, generally designated 32, for receiving urine. The flow-through sensing portion 32 includes a reservoir 34, and a flow-restricting drain aperture 36 for the reservoir 34.

Overflow apertures 38 are provided on the walls of the funnel 26 between the mouth 28 and apex 30, and baffles 40 are provided over the overflow apertures 38 to initially direct urine towards the flow-through sensing portion 32. The baffles 40 may all be a portion of a single annular baffle ring.

Finally, positioned within the reservoir 34 is a relatively small electrical temperature-sensing element 42 suitably electrically insulated and connected by means of lead wires 44 to the signal-processing subsystem 18. The temperature-sensing element 42 must be small enough to fit in the space available and to remain covered with urine during use. Further, the temperature-sensing element preferably has a relatively short thermal time constant (equivalent to low thermal mass) so that temperature readings can be taken quickly. For example, one suitable from of temperature-sensing element 42 reaches thermal equilibrium in the order of less than five seconds. Any known form of specific sensor may be employed for the element 42, such as a junction-type thermocouple or a thermistor.

In the operation of the form of device 20, urine is directed into the reservoir 34 where it contacts the temperature sensing element 42. Excess urine is lost through the overflow apertures 38, but only after the urine has had a chance to contribute to the reservoir 34 through action of the baffles 40. For accurate temperature measurement, a slight continuous flow is maintained past the temperature-sensing element 42 by virtue of the drain aperture 36.

Eventually, the entire funnel 26 is emptied, through the drain aperture 36.

Preferably, the device 20 is designed to retract under the toilet seat when not in use, and may be cleaned by the flushing action of the toilet.

Figure 3:
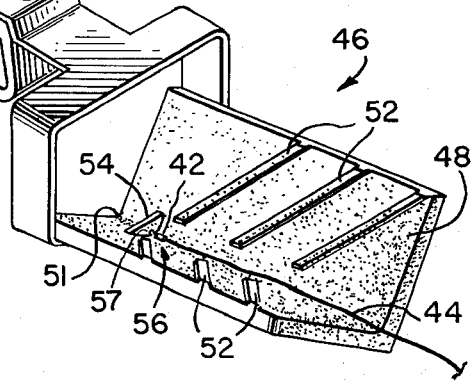
FIG. 3 depicts another form of temperature measurement device.

FIG. 3 depicts another specific form of temperature measuring device 46, which may be employed as an alternative to the device 20 of FIGS. 1 and 2. In general, the FIG. 3 device 46 provides improved results over the FIG. 2 device 20 due to the minimizing of evaporative and conductive cooling.

In overall configuration, the device 46 of FIG. 3 comprises an inclined V-trough 48 having sidewalls of thermally insulative material, for example, styrofoam one centimeter thick. A clamping device 50 is provided for securing the V-trough 48 within a toilet bowl, at an incline angle of approximately 24°. The clamp 50 may be secured to the front of the bowl, and the V-trough directed anteriorly.

The temperature-sensing element 42 again comprises a thermocouple, positioned in and generally at the downstream end 51 of the inclined V-trough 48. A plurality of ridges 52 are provided on the V-trough sidewalls for directing urine towards and over the temperature sensing element 42. In order to ensure that the temperature-sensing element 42 is completely covered during use, a small dam 54 is positioned generally at the downstream end of the V-trough 48. The dam 54 is relatively low in height compared to the sidewalls of the V-trough 48, the dam 54 thus defining an overflow reservoir 56. To allow the reservoir 56 to completely drain after use, a small drain aperture 57 is provided at the lower end of the dam 54.

Under some circumstances, the ridges 52 are sufficient, and the dam 54 is unnecessary. What is important is that the temperature-sensing element 42 remain completely immersed during a temperature measurement. This is particularly important due to the low thermal mass of the temperature-sensing element 42 inasmuch as even momentary exposure to ambient air can disturb the temperature reading. For this reason, then, it is generally preferred to include the dam 54.

While specific embodiments of the invention have been illustrated and described herein, it is realized that numerous modifications and changes will occur to those skilled in the art. It is therefore to be understood that the appended claims are intended to cover all such modifications and changes as fall within the true spirit and scope of the invention.

What is claimed is:

1. A system for use by a human female on a daily basis upon awakening for the purpose of detecting an upward shift in basal body temperature indicative of the beginning of a period of infertility, said system comprising:

a device for measurement of urine temperature upon micturation as an indicator of body temperature, said device including an electrical temperature-sensing element;

a signal-processing subsystem electrically connected to said temperature-sensing element and operable to record daily urine temperature readings indicative of basal body temperature, to perform a statistical test for recognizing an upward shift in basal body temperature indicative of the beginning of a period of infertility, and to signal when the statistical test has been satisfied;

said device for measurement of urine temperature including a funnel having a mouth for receiving urine and an apex, a flow-through sensing portion positioned at said funnel apex for receiving urine, said flow-through sensing portion including a reservoir, and a flow-restricting drain aperture for said reservoir; and said electrical temperature sensing element being positioned within said reservoir.

2. A system in accordance with claim 1, which further comprises at least one overflow aperture for said funnel between said funnel mouth and apex, and a baffle for said overflow aperture to initially direct urine towards said flow-through sensing portion.

3. A system for use by a human female on a daily basis upon awakening for the purpose of detecting an upward shift in basal body temperature indicative of the beginning of a period of infertility, said system comprising:

a device for measurement of urine temperature upon micturation as an indicator of body temperature, said device including an electrical temperature-sensing element;

a signal-processing subsystem electrically connected to said temperature-sensing element and operable to record daily urine temperature readings indicative of basal body temperature, to perform a statistical test for recognizing an upward shift in basal body temperature indicative of the beginning of a period of infertility, and to signal when the statistical test has been satisfied;

said device for measurement of urine temperature including an inclined V-trough having sidewalls of thermally insulative material, and a dam positioned generally at the downstream end of said inclined V-trough, said dam being relatively low in height compared to the sidewalls of said V-trough, said dam defining an overflow reservoir; and said electrical temperature-sensing element being positioned within said reservoir.

4. A system in accordance with claim 3, which further comprises a plurality of ridges on the V-trough sidewalls for directing urine towards said reservoir.

5. A system for use by a human female on a daily basis upon awakening for the purpose of detecting an upward shift in basal body temperature indicative of the beginning of a period of infertility, said system comprising:

a device for measurement of urine temperature upon micturation as an indicator of body temperature, said device including an electrical temperature-sensing element;

a signal-processing subsystem electrically connected to said temperature-sensing element and operable to record daily urine temperature readings indicative of basal body temperature, to perform a statistical test for recognizing an upward shift in basal body temperature indicative of the beginning of a period of infertility, and to signal when the statistical test has been satisfied; and said device for measurement of urine temperature including an inclined V-trough having sidewalls of thermally insulative material, said electrical temperature sensing element being positioned in and generally at the downstream end of said inclinded V-trough, and a plurality of ridges on the V-trough sidewalls for directing urine towards and over said electrical temperature-sensing element.

6. A device for measurement of urine temperature upon micturation as an indicator of body temperature, said device comprising;

a funnel having a mouth for receiving urine and an apex; and a flow-through sensing portion positioned at said funnel apex for receiving urine, said flow-through sensing portion including a reservoir, a flow-restricting drain aperture for said reservoir, and an electrical temperature-sensing element within said reservoir.

7. A device in accordance with claim 6, which further comprises at least one overflow aperture for said funnel between said funnel mouth and apex, and a baffle for said overflow aperture to initially direct urine towards said flow-through sensing portion.

8. A device in accordance with claim 7, wherein said electrical temperature-sensing element has a thermal time constant of less than twenty seconds.

9. A device in accordance with claim 8, wherein said electrical temperature-sensing element comprises a junction-type thermocouple.

10. A device in accordance with claim 7, which further comprises a support structure for positioning said funnel and flow-through sensing portion within a toilet bowl.

11. A device in accordance with claim 7, wherein said temperature-sensing element is adapted for connection to a signal-processing system for detecting an upward shift in basal body temperature indicative of the beginning of a period of infertility when said device is employed by a human female on a daily basis upon awakening.

12. A device in accordance with claim 6, which further comprises a support structure for positioning said funnel and flow-through sensing portion within a toilet bowl.

13. A device in accordance with claim 6, wherein said temperature-sensing element is adapted for connection to a signal-processing system for detecting an upward shift in basal body temperature indicative of the beginning of a period of infertility when said device is employed by a human female on a daily basis upon awakening.

14. A device in accordance with claim 13, wherein said electrical temperature-sensing element has a thermal time constant of less than twenty seconds.

15. A device in accordance with claim 6, wherein said temperature-sensing element is adapted for connection to a signal-processing system for detecting an upward shift in basal body temperature indicative of the beginning of a period of infertility when said device is employed by a human female on a daily basis upon awakening.

16. A device for measurement of urine temperature upon micturation as an indicator of body temperature, said device comprising:

an inclined V-trough having sidewalls of thermally insulative material;

a dam positioned generally at the downstream end of said inclined V-trough, said dam being relatively low in height compared to the sidewalls of said V-trough, and said dam defining an overflow reservoir; and an electrical temperature-sensing element within said reservoir.

17. A device in accordance with claim 16, which further comprises a plurality of ridges on the V-trough sidewalls for directing urine towards said reservoir.

18. A device in accordance with claim 17, which further comprises a support structure for positioning said inclined V-trough within a toilet bowl.

19. A device in accordance with claim 18, wherein said temperature-sensing element is adapted for connection to a signal-processing system for detecting an upward shift in basal body temperature indicative of the beginning of a period of infertility when said device is employed by a human female on a daily basis upon awakening.

20. A device in accordance with claim 17, wherein said temperature-sensing element is adapted for connection to a signal-processing system for detecting an upward shift in basal body temperature indicative of the beginning of a period of infertility when said device is employed by a human female on a daily basis upon awakening.

21. A device in accordance with claim 16, wherein said electrical temperature-sensing element has a thermal time constant of less than twenty seconds.

22. A device in accordance with claim 21, wherein said electrical temperature-sensing element comprises a junctiontype thermocouple.

23. A device in accordance with claim 16, which further comprises a support structure for positioning said inclined V-trough within a toilet bowl.

24. A device in accordance with claim 16, wherein said temperature-sensing element is adapted for connection to a signal-processing system for detecting an upward shift in basal body temperature indicative of the beginning of a period of infertility when said device is employed by a human female on a daily basis upon awakening.

25. A device in accordance with claim 24, wherein said electrical temperature-sensing element has a thermal time constant of less than twenty seconds.

26. A device for measurement of urine temperature upon micturation as an indicator of body temperature, said device comprising:
- an inclined V-trough having sidewalls of thermally insulative material;
- an electrical temperature-sensing element positioned in and generally at the downstream end of said inclined V-trough; and
- a plurality of ridges on the V-trough sidewalls for directing urine towards and over said electrical temperature-sensing element.

27. A device in accordance with claim 26, wherein said electrical temperature-sensing element has a thermal time constant of less than twenty seconds.

* * * * *